United States Patent
Miesel

(10) Patent No.: US 9,278,176 B2
(45) Date of Patent: Mar. 8, 2016

(54) DUAL PLUNGER BASED SYSTEMS AND METHOD FOR USE IN DETERMINING A VOLUME IN A RESERVOIR

(71) Applicant: Medtronic, Inc., Minneapolis, MN (US)

(72) Inventor: Keith A. Miesel, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 199 days.

(21) Appl. No.: 14/177,982

(22) Filed: Feb. 11, 2014

(65) Prior Publication Data

US 2014/0163524 A1    Jun. 12, 2014

Related U.S. Application Data

(63) Continuation of application No. PCT/US2012/058614, filed on Oct. 4, 2012, which is a continuation of application No. 13/269,088, filed on Oct. 7, 2011, now Pat. No. 8,561,460.

(51) Int. Cl.

| | |
|---|---|
| *G01F 17/00* | (2006.01) |
| *A61M 5/168* | (2006.01) |
| *A61M 5/142* | (2006.01) |
| *G01F 23/14* | (2006.01) |
| *A61M 5/14* | (2006.01) |

(52) U.S. Cl.
CPC ......... *A61M 5/1684* (2013.01); *A61M 5/14276* (2013.01); *G01F 17/00* (2013.01); *G01F 23/14* (2013.01); *A61M 5/14* (2013.01); *A61M 2205/3317* (2013.01)

(58) Field of Classification Search
CPC .......... A61M 2205/3317; A61M 5/14; A61M 5/14276; A61M 5/1684; A61M 5/1685; G01F 17/00; G01F 23/14
See application file for complete search history.

(56) References Cited

U.S. PATENT DOCUMENTS

| | | |
|---|---|---|
| 3,293,916 A | 12/1966 | Goff |
| 4,193,397 A | 3/1980 | Tucker et al. |
| 5,507,737 A | 4/1996 | Palmskog |

(Continued)

FOREIGN PATENT DOCUMENTS

| | | |
|---|---|---|
| EP | 1048309 A2 | 11/2000 |
| WO | WO-2007127828 A2 | 11/2007 |
| WO | WO-2013052579 A1 | 4/2013 |

OTHER PUBLICATIONS

International Search Report and Written Opinion mailed Jan. 24, 2013 for PCT/US2012/058614 claiming benefit of U.S. Appl. No. 13/269,088, filed Oct. 7, 2011.

*Primary Examiner* — Peter Macchiarolo
*Assistant Examiner* — Natalie Huls
(74) *Attorney, Agent, or Firm* — Harness, Dickey & Pierce, P.L.C.

(57) ABSTRACT

A system, for use in determining a volume in a reservoir, includes a bulkhead, a plunger assembly, and a base. The plunger assembly is connected to the bulkhead. The plunger assembly includes a first plunger and a second plunger. The first plunger has a corresponding first biasing member. The second plunger has a corresponding second biasing member. The base of the reservoir is connected to the first plunger. Movement of the base causes compression or expansion of the first biasing member, which causes compression or expansion of the second biasing member. The bulkhead, the first plunger, and the base define a first portion of the reservoir. Positions of the first plunger and the base, relative to the bulkhead, are based on the volume in the reservoir.

29 Claims, 10 Drawing Sheets

(56) References Cited

U.S. PATENT DOCUMENTS

| | | |
|---|---|---|
| 6,152,898 A | 11/2000 | Olsen |
| 6,228,050 B1 | 5/2001 | Olsen et al. |
| 6,482,182 B1 | 11/2002 | Carroll et al. |
| 6,493,573 B1 | 12/2002 | Martinelli et al. |
| 6,516,212 B1 | 2/2003 | Bladen et al. |
| 7,104,767 B2 | 9/2006 | Lee |
| 7,392,666 B2 | 7/2008 | Namiki |
| 7,867,221 B2 | 1/2011 | Haase |
| 8,083,730 B2 | 12/2011 | Miesel |
| 8,397,578 B2 | 3/2013 | Miesel et al. |
| 8,561,460 B2 * | 10/2013 | Miesel ............... A61M 5/1684 604/132 |
| 2002/0173773 A1 | 11/2002 | Olsen |
| 2003/0114752 A1 | 6/2003 | Henderson et al. |
| 2005/0049486 A1 | 3/2005 | Urquhart et al. |
| 2005/0085714 A1 | 4/2005 | Foley et al. |
| 2005/0085720 A1 | 4/2005 | Jascob et al. |
| 2006/0282040 A1 | 12/2006 | Toman et al. |
| 2007/0255259 A1 | 11/2007 | Miesel |
| 2007/0255260 A1 | 11/2007 | Haase |
| 2011/0208163 A1 | 8/2011 | Miesel |
| 2011/0301575 A1 | 12/2011 | Miesel et al. |
| 2012/0017689 A1 | 1/2012 | Giordano et al. |
| 2012/0109099 A1 | 5/2012 | Rogers et al. |
| 2012/0283639 A1 | 11/2012 | Ali et al. |
| 2012/0303000 A1 | 11/2012 | Olsen |

* cited by examiner

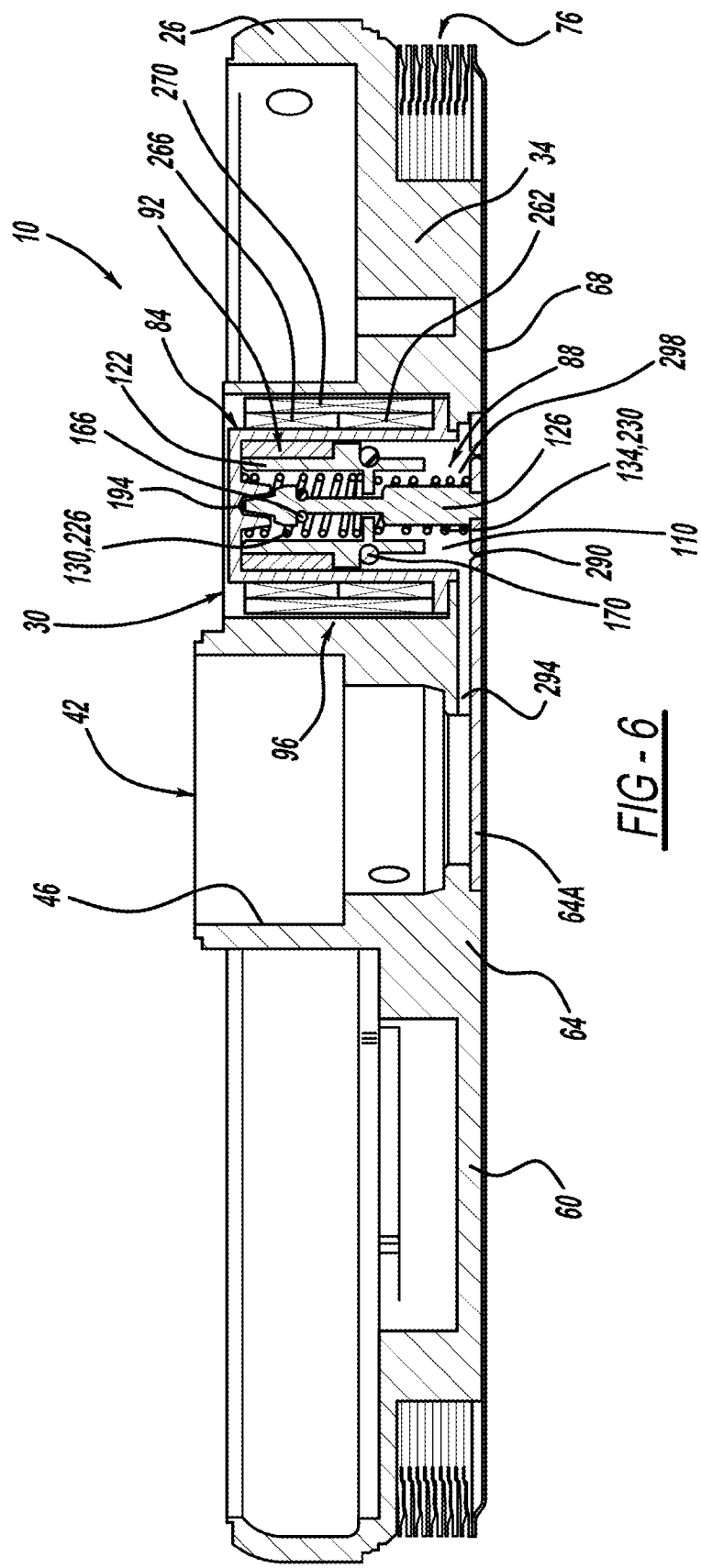

DUAL PLUNGER BASED SYSTEMS AND METHOD FOR USE IN DETERMINING A VOLUME IN A RESERVOIR

CROSS REFERENCE TO RELATED APPLICATIONS

This application is a continuation of International PCT Application PCT/US2012/058614, filed on Oct. 4, 2012 and published in English as WO/2013/052579 on Apr. 11, 2013. This application claims priority to U.S. patent application Ser. No. 13/269,088 filed on Oct. 7, 2011. The disclosures of the above applications are incorporated herein by reference.

FIELD

The present disclosure relates generally to a ratiometric plunger assembly for volume sensing applications including, but not limited to, volume sensing in an implantable infusion device.

BACKGROUND

This section provides background information related to the present disclosure that is not necessarily prior art.

Medical devices, such as medical pumps, can be used to treat a variety of physiological, psychological, and emotional conditions. For some medical conditions, medical pumps can assist an individual in overcoming such conditions. For example, medical pumps may be used for chronic delivery of therapeutic agents, such as drugs. As one specific example, a medical pump may be used to deliver insulin to a diabetic patient. Other examples include delivery of pain relief medication, e.g., to the intrathecal or epidural space of a patient, to alleviate chronic pain.

Some medical pumps are wholly implantable. Implantable medical pumps may be implanted at a location in the body of a patient and deliver a fluid medication through a catheter to a selected delivery site within the body of the patient. Typically, the catheter connects to an outlet of the medical pump and delivers a therapeutic agent at a programmed infusion rate to a predetermined location to treat a medical condition. An implantable medical pump is implanted by a clinician into a patient at a location that interferes as little as practicable with patient activity. For example, implantable medical pumps are often implanted subcutaneously in the lower abdomen of a patient. Implantable medical pumps may include self-sealing fluid reservoirs accessible through ports to facilitate in-service refilling by percutaneous injection.

SUMMARY

This section provides a general summary of the disclosure, and is not a comprehensive disclosure of its full scope or all of its features.

A system for use in determining a volume in a reservoir is provided. The system includes a bulkhead, a plunger assembly, and a base. The plunger assembly is connected to the bulkhead. The plunger assembly includes a first plunger and a second plunger. The first plunger has a corresponding first biasing member. The second plunger has a corresponding second biasing member. The base of the reservoir is connected to the first plunger. Movement of the base causes compression or expansion of the first biasing member, which causes compression or expansion of the second biasing member. The bulkhead, the first plunger, and the base define a first portion of the reservoir. Positions of the first plunger and the base, relative to the bulkhead, are based on the volume in the reservoir.

In other features, a method for use in determining a volume in a reservoir is provided. The method includes: transferring a fluid between a fill port and the reservoir; moving a base of the reservoir based on the transfer of the fluid; based on the movement of the base, displacing a first plunger connected to the base, where the first plunger has a corresponding first biasing member; and based on movement of the first plunger, displacing a second plunger having a corresponding second biasing member. The movement of the base causes compression or expansion of the first biasing member, which causes compression or expansion of the second biasing member. A bulkhead, the first plunger, and the base define a first portion of the reservoir. Positions of the first plunger and the base, relative to the bulkhead, are based on the volume in the reservoir.

In other features, a system for determining a volume in a reservoir is provided. The system includes a sensor assembly and a circuit. The sensor assembly includes a first plunger, a second plunger and a base of the reservoir. The first plunger includes a first sealing member and having a corresponding first biasing member. The second plunger is disposed in a cavity. The second plunger includes a second sealing member and has a corresponding second biasing member. A portion of the second plunger is disposed between the first biasing member and the second biasing member. The volume in the reservoir varies. The first plunger is connected to the base and is configured to move with the base. The circuit is configured to generate position information indicating a position of a target based on operation of the sensor assembly. The target is connected to the second plunger. A position of the base relative to a bulkhead is representative of the volume in the reservoir. The circuit is configured to move the first sealing member and the second sealing member into sealing positions to seal off fluid communication between (i) a fill port, and (ii) the reservoir or the cavity. The reservoir is in a full state when the first sealing member and the second sealing member are in the sealing positions.

In one form, a volume sensing system for use in determining a volume of a variable volume reservoir is provided in accordance with various aspects of the present teachings. The system can include a plunger assembly having lower and upper plungers and lower and upper biasing members. The lower plunger can have a first end and an opposite second end, where the first end can be adapted to move with a bottom of the reservoir. The upper plunger can have a first end and an opposite second end, where the upper plunger can be slidable relative to the lower plunger. The lower biasing member can be positioned substantially between a base of the reservoir and the upper plunger, and the upper biasing member can be adapted to be positioned between the upper plunger and an interference member. The upper biasing member can be configured to have a predetermined stiffness relative to the lower biasing member such that upon movement of the lower plunger in a first direction, the upper plunger can be configured to move in the first direction at a predetermined fraction of the amount of movement of the lower plunger. The predetermined fraction of the amount of movement can be determined at least in part by the predetermined stiffness of the upper biasing member relative to the lower biasing member, wherein a position of the upper plunger can be adapted to be correlated to a corresponding volume of the reservoir.

In another form, a volume sensing system for use in determining a volume of a variable volume reservoir is provided in accordance with various aspects of the present teachings. The system can include a housing and a volume sensor assembly. The housing can maintain the variable volume reservoir and can include a bulkhead. The bulkhead can define in part a top of the variable volume reservoir and an internal passage open to the reservoir. The variable volume reservoir can include a base wall that is movable relative to the bulkhead, wherein a volume of an internal region of the reservoir can be a function of a distance between the base wall and the bulkhead. The volume sensor assembly can generate information indicative of a current volume of the internal region and can include a plunger assembly, a ferromagnetic target and circuitry. The plunger assembly can include lower and upper plungers and lower and upper biasing members. The lower plunger can have a first end and an opposite second end, where the first end can be coupled to the base wall. The upper plunger can have a first end and an opposite second end facing the base wall, where the upper plunger can be slidably coupled to the lower plunger. The lower biasing member can be positioned substantially between the base wall and the upper plunger, and the upper biasing member can be positioned substantially between the upper plunger and a closed end of the internal passage. The upper biasing member can be configured to have a predetermined stiffness relative to the lower biasing member such that upon movement of the lower plunger in a first direction, the upper plunger is configured to move in the first direction at a predetermined fraction of the amount of movement of the lower plunger. The ferromagnetic target can be coupled to the upper plunger and moveable therewith relative to the internal passage. The circuitry can be associated with the internal passage and can be configured to detect a longitudinal position of the target relative to the internal passage. The longitudinal position of the target relative to the internal passage can be representative of a volume of the internal region of the reservoir.

In yet another form, a method for use in determining a volume of a variable volume reservoir is provided in accordance with various aspects of the present teachings. The method can include generating position information of a target coupled to an upper plunger through operation of a volume sensor assembly. The upper plunger can be coupled to a lower plunger and positioned between an upper biasing member and a lower biasing member. The lower plunger can be coupled to a base of the reservoir and can be configured for movement therewith. A position of the base relative to a housing associated with the variable volume reservoir can be representative of a volume of an internal region of the reservoir. First and second sealing members associated with the respective lower and upper plungers can be moved into sealing positions to seal off fluid communication between a fill port defined by the housing when the reservoir is in a full condition. The fill port can be in selective fluid communication with the internal region of the reservoir.

Further areas of applicability will become apparent from the description provided herein. The description and specific examples in this summary are intended for purposes of illustration only and are not intended to limit the scope of the present disclosure.

DRAWINGS

The present teachings will become more fully understood from the detailed description, the appended claims and the following drawings. The drawings are for illustrative purposes only of selected embodiments and not all possible limitations, and are not intended to limit the scope of the present disclosure.

Figure 4:
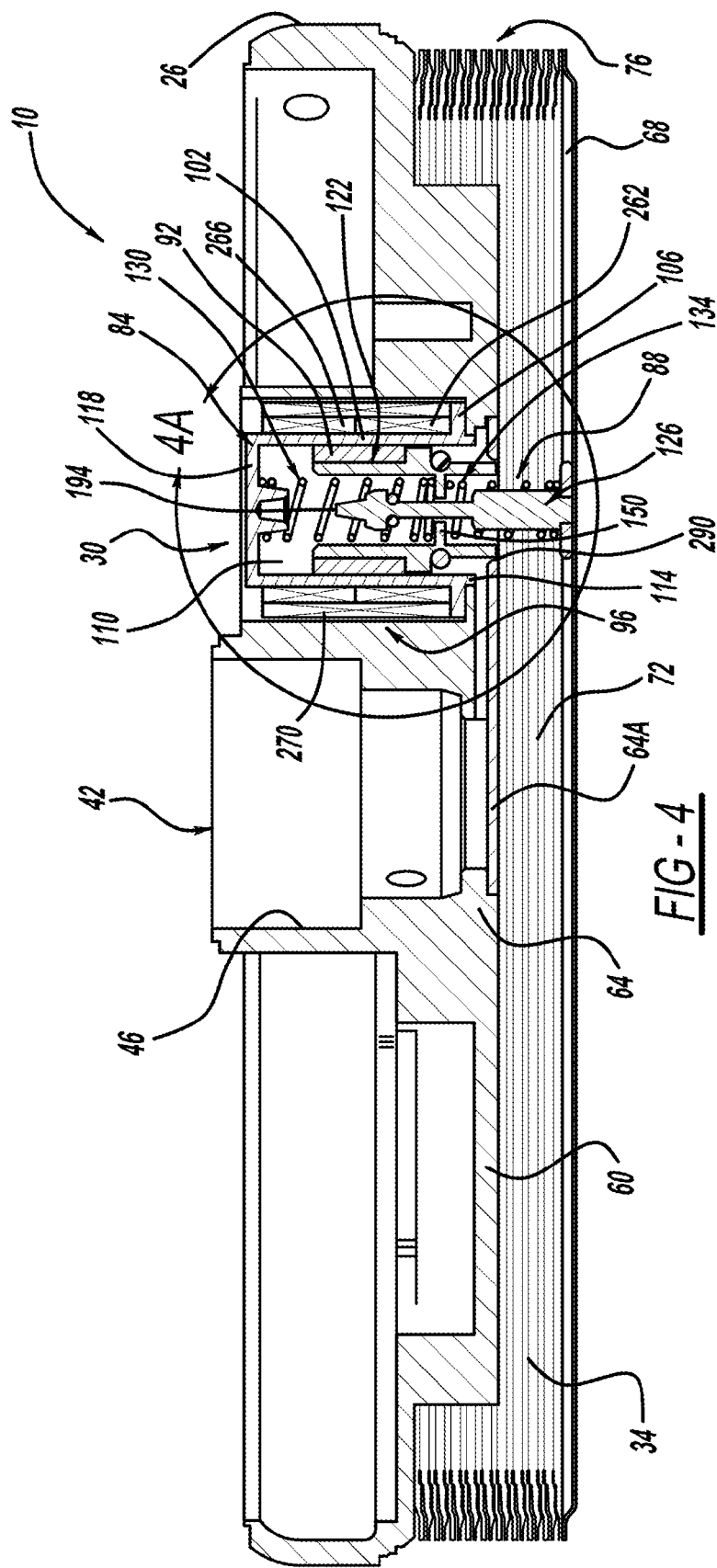
FIG. 4 is cross-sectional view taken along line 4-4 of the implantable infusion device of FIG. 2 illustrating a volume sensing assembly and a reservoir in an exemplary partially full condition in accordance with the teachings of the present disclosure.
Figure 9:
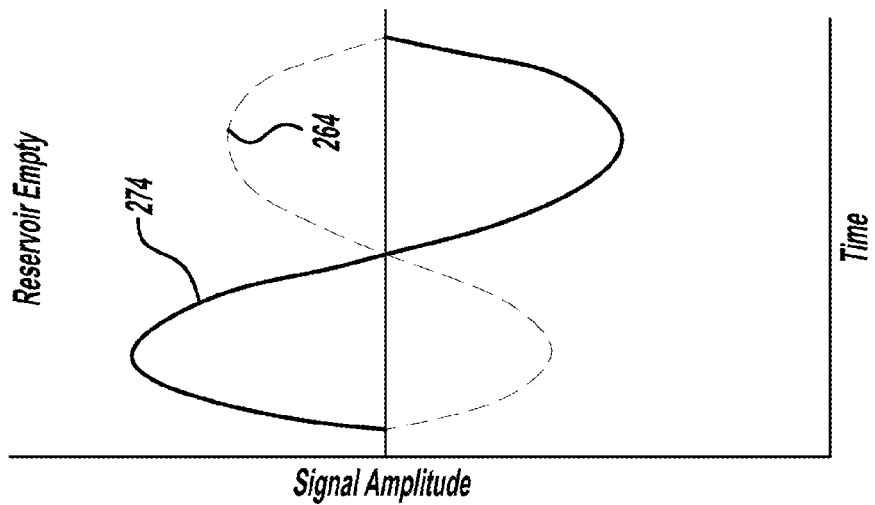
Figure 8:
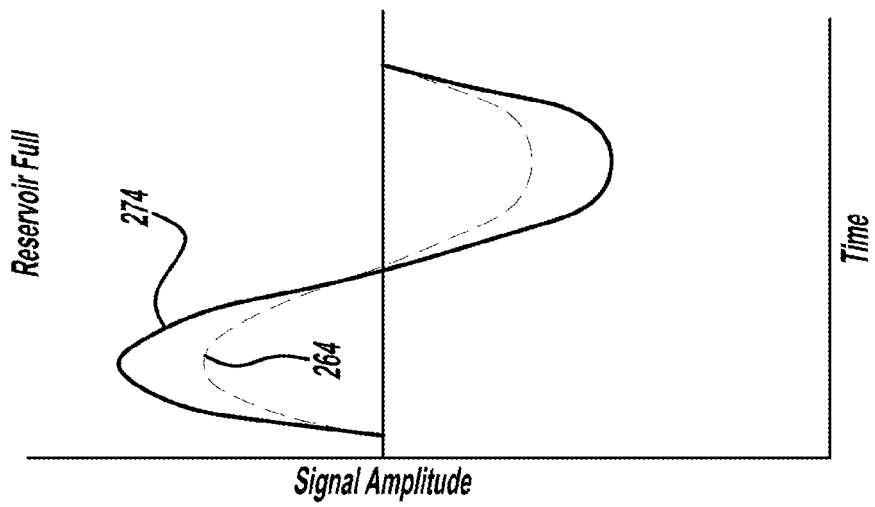
Figure 7:
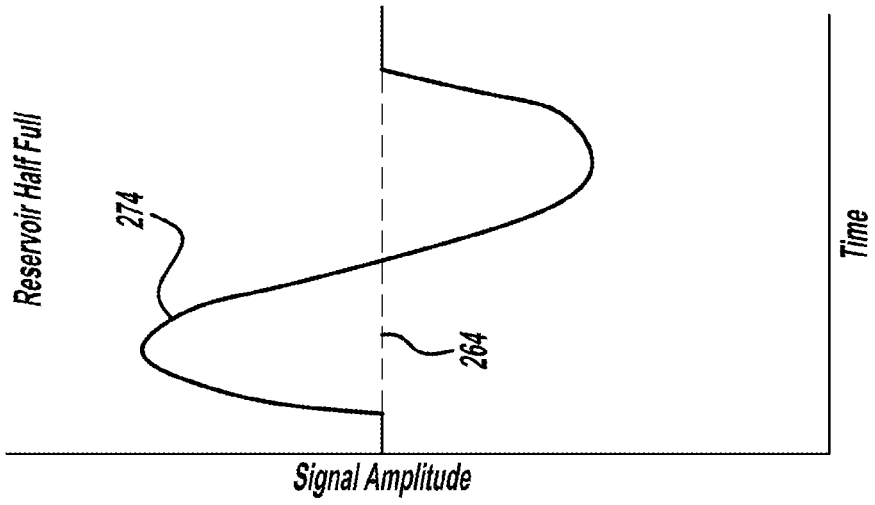

FIG. 6 is a similar cross-sectional view of the implantable infusion device of FIG. 4 illustrating the volume sensing assembly and the reservoir in an exemplary empty condition in accordance with the teachings of the present disclosure; and FIGS. 7-9 are diagrammatic views of exemplary operational characteristics of primary and secondary coils of the volume sensing assembly in accordance with the teachings of the present disclosure.

DETAILED DESCRIPTION

The following description is merely exemplary in nature and is not intended to limit the present disclosure, its application, or uses. It should be understood that throughout the drawings, corresponding reference numerals indicate like or corresponding parts and features with the various elements in each view being drawn to scale. Although the following description is related generally to a volume sensing assembly for implantable infusion devices, such as implantable medical or drug pumps for use in delivering a therapeutic substance or agent to a patient, it should be appreciated that the volume sensing assembly and associated telescoping plunger assembly discussed herein can be applicable to other medical devices including, but not limited to, non-implantable medical pumps or other medical devices configured to contain a fluid therein.

Exemplary embodiments are provided so that this disclosure will be thorough, and will fully convey the scope to those who are skilled in the art. Numerous specific details are set forth such as examples of specific components, devices, systems and/or methods, to provide a thorough understanding of exemplary embodiments of the present disclosure. It will be apparent to those skilled in the art that specific details need not be employed, that exemplary embodiments may be embodied in many different forms and that neither should be construed to limit the scope of the disclosure. In some exemplary embodiments, well-known processes, well-known device structures, and well-known technologies are not described in detail.

Figure 1:
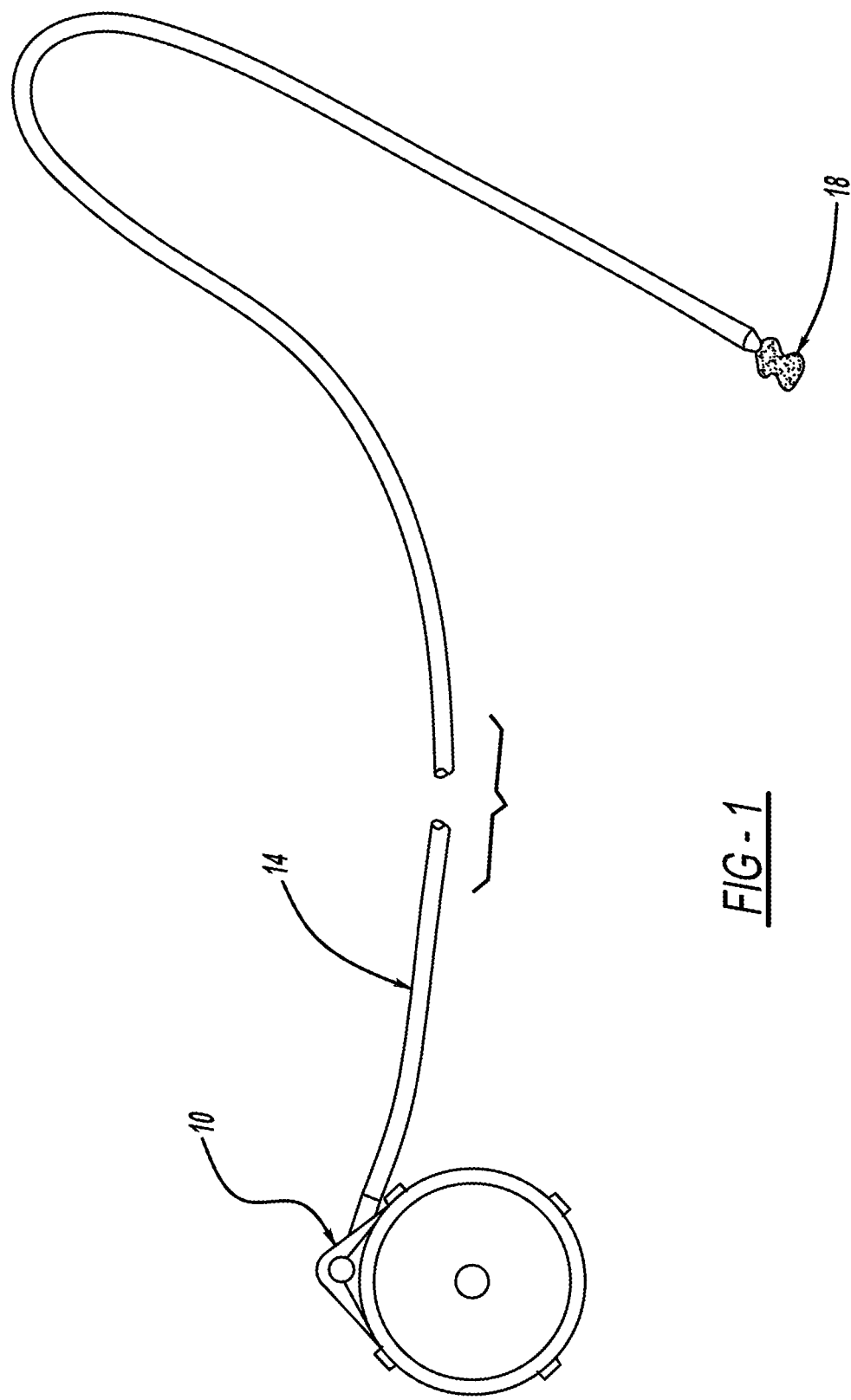
FIG. 1 is a diagram illustrating an exemplary fluid delivery system, which includes an implantable infusion device in accordance with the teachings of the present disclosure along with a delivery catheter.
Figure 2:
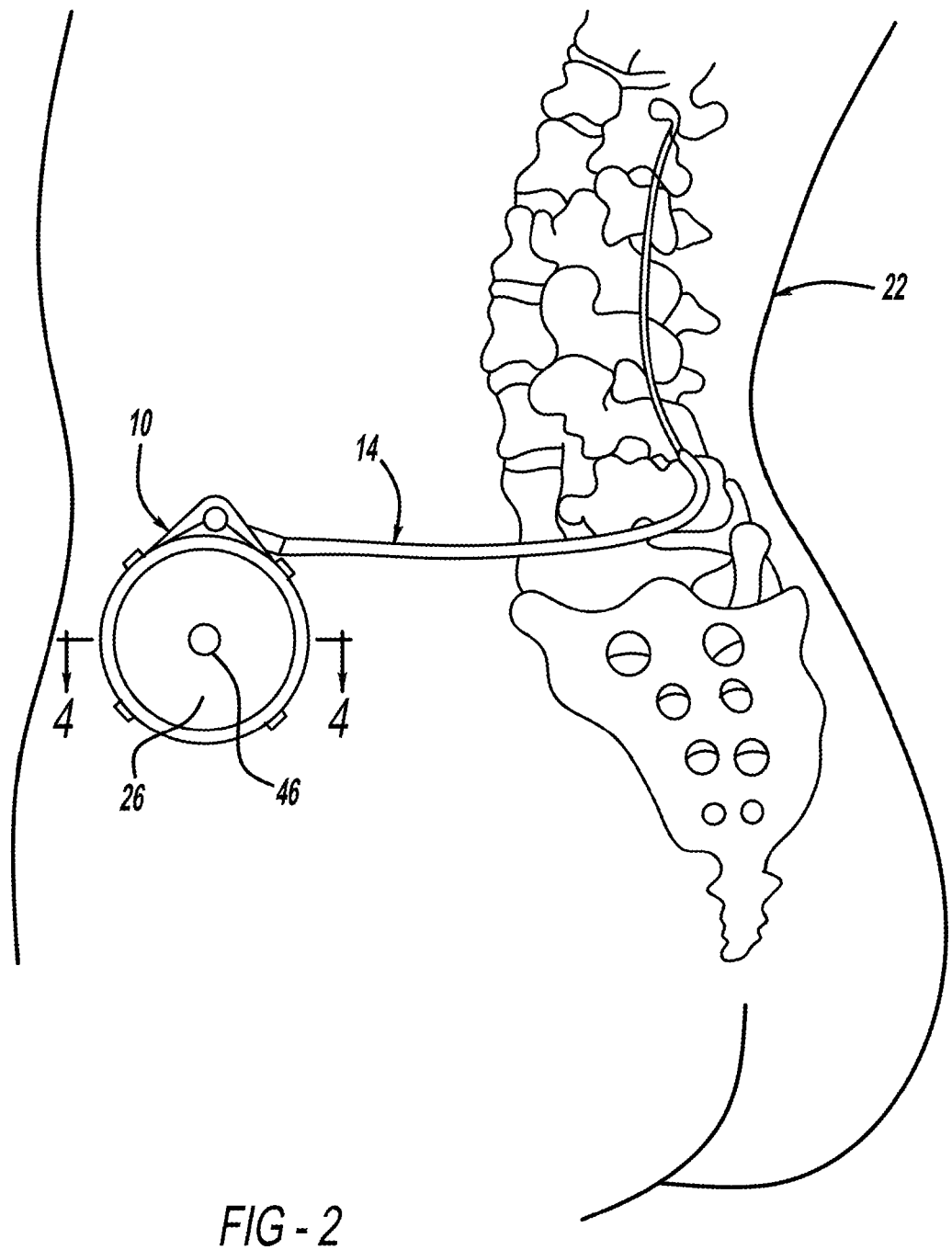
FIG. 2 is a diagram of the implantable infusion device and delivery catheter of FIG. 1 configured to deliver a therapeutic agent or substance to a patient.

Turning now to FIGS. 1-2, an overview of an exemplary implantable infusion device 10 is shown operatively associated with an intrathecal delivery catheter 14. In general terms, the implantable infusion device 10, also known as an implantable drug pump, medical pump or therapeutic substance delivery device, can assume a variety of forms, and can be provided as part of an intrathecal infusion system that further includes an external programmer (not shown), for example as provided with a SynchroMed® EL Infusion System available from Medtronic, Inc., of Minneapolis, Minn. Regardless, the implantable infusion device 10 can operate to infuse a therapeutic fluid or substance 18 (drawn generally in FIG. 1) into a patient 22 via the delivery catheter 14. The therapeutic substance 18 can be any infusion agent, product, or fluid substance intended to have a therapeutic effect, such as pharmaceutical compositions, genetic materials, biologics, and others (e.g., insulin, saline solution, fluoroscopy agents, etc.).

Figure 3:
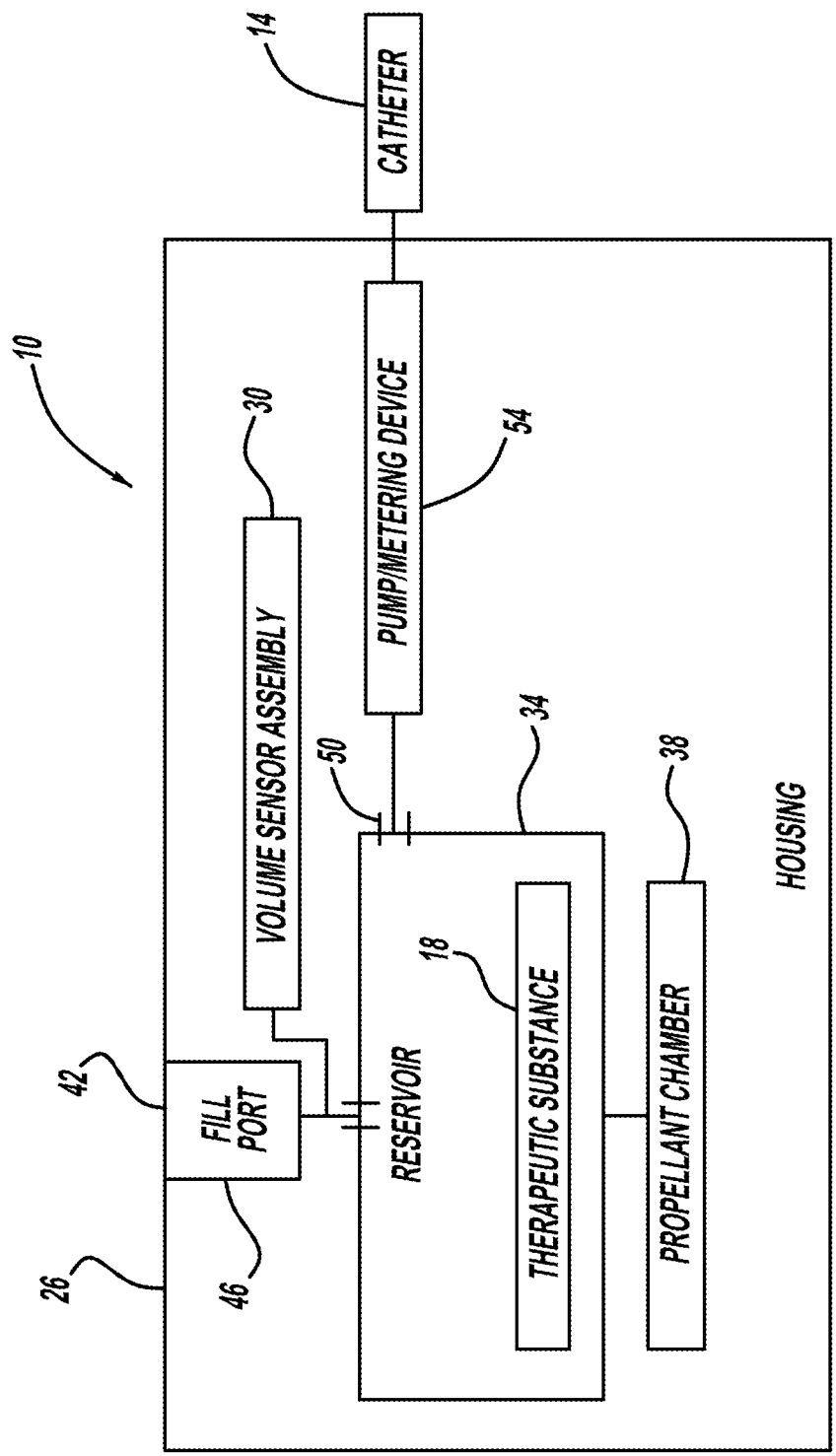
FIG. 3 is a simplified functional block diagram of the implantable infusion device in accordance with the teachings of the present disclosure.

With additional reference to FIG. 3, the implantable infusion device 10 can include a housing 26 and a volume sensor assembly 30. The housing 26 can define in part, a reservoir 34 for containing the therapeutic substance 18 and can define a variable volume, as discussed below. In some embodiments, a propellant chamber 38 can be provided, formed against the reservoir 34, and serving to place a constant positive pressure on to the reservoir 34. The therapeutic substance 18 can be filled into the reservoir 34 via an inlet 42 (e.g., a fill/refill port 46 including a septum), and can release the therapeutic substance 18 via an outlet 50. In this regard, the implantable infusion device 10 can include a pump mechanism and/or metering device 54 in some embodiments that dictates the amount or volume of the therapeutic substance 18 to be drawn from the reservoir 34. To this end, the pump mechanism 54 can assume a wide variety of forms as is known in the art. Regardless, the outlet 50 can be fluidly connected to the delivery catheter 14 for subsequent delivery of a desired amount of the therapeutic substance 18 from the outlet 50 to the patient 22. As will be discussed in greater detail below, the volume sensor assembly 30 can be maintained by housing 26 and configured to sense information indicative of a volume of the reservoir 34, and thus indicative of a volume of the therapeutic substance 18 contained within the reservoir 34. As will also be discussed below, the volume sensor assembly 30 can include an upper member that can telescopically travel at a predetermined fraction of an amount of travel of an associated lower member thereby providing for a lower profile or more compact implantable infusion device 10. The volume sensor assembly 30 can also cooperate with housing 26 and fill port 46 to limit an amount of therapeutic substance 18 that can be supplied to reservoir 34 to prevent overfilling of reservoir 34.

The implantable infusion device 10 can incorporate a number of features not otherwise described or illustrated in the figures. For example, a power source (not shown) can be provided as part of the pump mechanism 54 along with an electronics module or controller, such as with a positive or peristaltic configuration. Alternatively, the implantable infusion device 10 can assume a passive infusion configuration whereby the propellant chamber 38 serves as a pump drive, with flow from the reservoir outlet 50 being passively controlled, in some embodiments, through capillary tubing (not shown) or similar structure(s) (akin, for example, to the IsoMed™ Implantable Constant-Flow Infusion Pump available from Medtronic, Inc., of Minneapolis, Minn.). Further, other programmable module(s) (not shown) can be included. Thus, the implantable infusion device 10 is not limited to the configuration represented in figures.

Figure 4A:
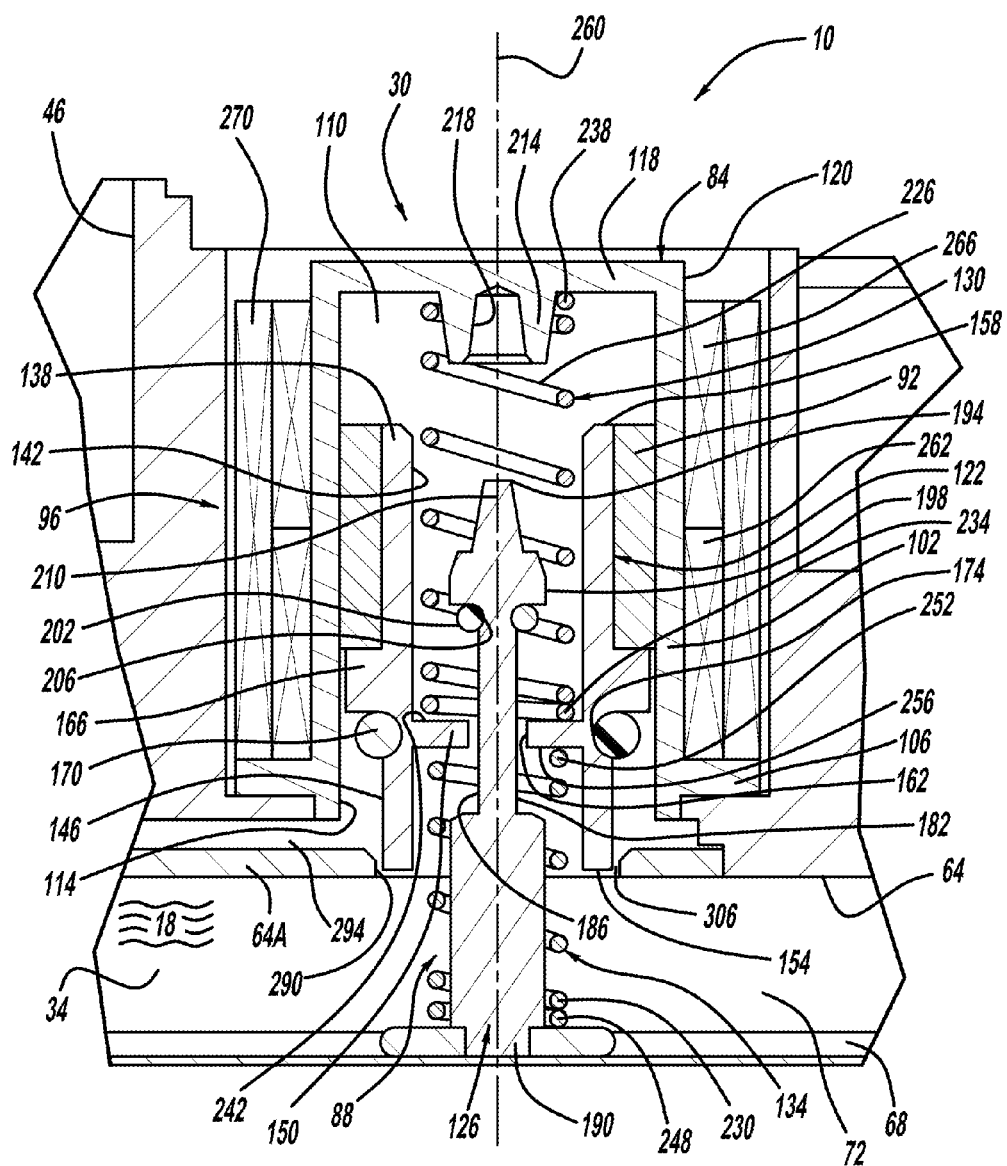
FIG. 4A is an enlarged view of a portion of the implantable infusion device of FIG. 4 in accordance with the teachings of the present disclosure.

With additional reference to FIGS. 4-9, and in particular FIG. 4A, the volume sensor assembly 30 and exemplary associated portions of the implantable infusion device 10 will now be discussed in greater detail. The housing 26 can include a stationary wall 60 with which the volume sensor assembly 30 can be associated. As a point of reference, the housing 26 can include a number of other walls; however, the stationary wall 60 with which the volume sensor assembly 30 is associated with can provide a consistent reference point relative to the reservoir 34. In some embodiments, the stationary wall 60 can form a part of the reservoir 34 (e.g., the stationary wall 60 can be a bulkhead 64 of the reservoir 34); in other embodiments the stationary wall 60 can be provided apart from the reservoir 34. Regardless, the reservoir 34 can be defined in part by a bottom or base wall 68 and can be fluidly coupled to the refill port 46 and outlet 50 (FIG. 3), as well as an internal region 72 within which the therapeutic substance 18 can be contained. In some embodiments, the base wall 68 can be formed as part of a bellows assembly 76 that otherwise translates a positive pressure onto the contained therapeutic substance 18. Alternatively, the reservoir 34 can be defined in a variety of other forms. However, the base wall 68 is movable relative to the bulkhead 64 such that the internal region 72 is variable. In other words, the reservoir 34 can have a variable volume dictated by a position of the base wall 68 relative to the bulkhead 64.

In some embodiments, the base wall 68 can be connected to the bulkhead 64 via the bellows assembly 76 such that the internal region 72 can increase in volume as the base wall 68 moves away from the bulkhead 64, such as during filling of reservoir 34 (and can decrease in volume as the base wall 68 moves towards the bulkhead 64). For example, in one embodiment, the propellant (not shown) within the propellant chamber 38 (FIG. 3) can assert a continuous, positive pressure onto the base wall 68, and thus onto the reservoir 34. Alternatively, and as previously described, the implantable infusion device 10 can be configured such that a powered mechanism is coupled to the base wall 68 (or a corresponding component) that otherwise dictates a position of the base wall 68 relative to the bulkhead 64.

Figure 5:
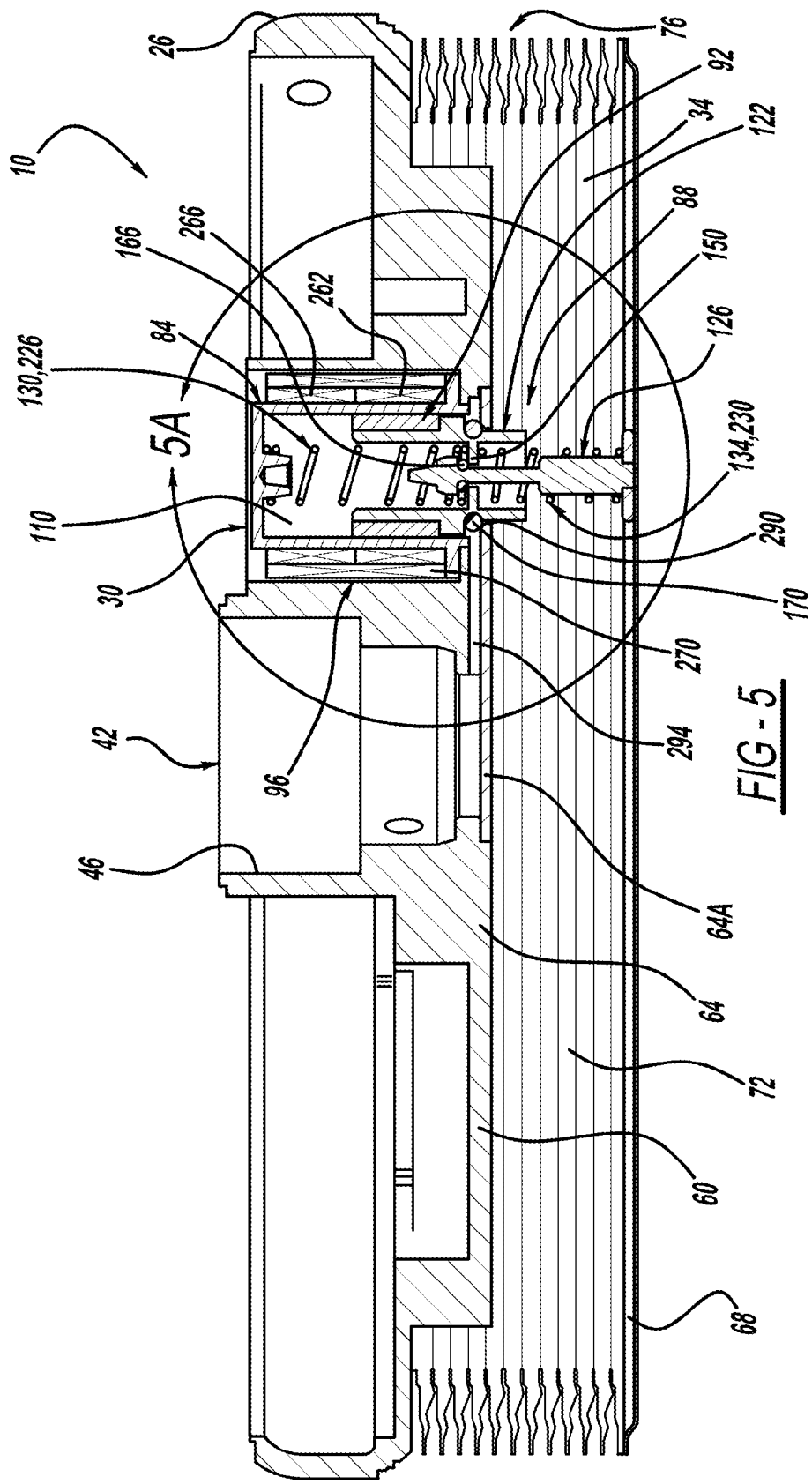
FIG. 5 is a similar cross-sectional view of the implantable infusion device of FIG. 4 illustrating the volume sensing assembly and the reservoir in an exemplary full condition in accordance with the teachings of the present disclosure.

Regardless of an exact configuration of the implantable infusion device 10, one exemplary embodiment of the volume sensor assembly 30 is shown in greater detail in FIGS. 4-6 and can include a cap member 84, a plunger assembly 88, a target or core 92, and volume detection circuitry 96 (referenced generally). In general terms, the plunger assembly 88 and target 92 can be configured to move longitudinally relative to the cap member 84 and circuitry 96 based on a change in volume of the internal region 72 of reservoir 34. The circuitry 96 can generate information indicative of a sensed longitudinal position of the target 92 and thereby a volume of reservoir 34, as will be discussed in greater detail below.

In one embodiment, the cap member 84 includes a tubular member 102 and a flange 106. The tubular member 102 can form a passage 110 extending from a first, open end 114 to a second, closed end 118. Further, the tubular member 102 can define an exterior surface 120 approximating a length of the passage 110. The flange 106 can be configured for sealed mounting to the bulkhead 64, extending in a generally radial fashion from the tubular member 102 at the open end 114. In one embodiment, the cap member 84 can be formed of a hardened, generally non-ferromagnetic material, for example titanium, capable of achieving a hermetic seal upon assembly to the bulkhead 64. In this regard, the cap member 84 can be mounted to the bulkhead 64 in a wide variety of fashions. For example, in one embodiment, the annular flange 106 can be welded to the bulkhead 64. In other embodiments, the flange 106 can be supported in part by an additional structural member, such as washer 64A. Regardless, upon final assembly, the cap member 84 can be assembled to the bulkhead 64 such that the passage 110, and in particular the open end 114, can be fluidly open to and in communication with the internal region 72 of reservoir 34. Thus, with the exemplary embodiment shown in FIGS. 4-6 in which the bulkhead 64 can form a portion of the reservoir 34, the passage 110 is fluidly open to and in communication with the internal region 72.

In one exemplary embodiment, the plunger assembly 88 can include a first or upper member 122 and a second or lower member 126 along with a first or upper biasing member 130 and a second or lower biasing member 134. In the exemplary embodiment illustrated in FIGS. 4-6, the upper member 122 can be in the form of a generally tubular member 138 having an inner surface 142 and an outer surface 146. The tubular member 138 can define an internal wall 150 positioned between a lower end 154 and an opposite upper end 158 of tubular member 138. In one exemplary embodiment, the internal annular wall 150 can define an aperture 162 configured to slidably receive a portion of the lower member 126 therethrough, as will be discussed in greater detail below. An annular flange 166 can extend radically outward from the outer surface 146 and can include a width or diameter complimentary to a corresponding width or diameter of cap member passage 110 such that lower member 126 can be slidably received in and moveable relative to passage 110. The outer surface 146 can carry a first sealing member 170 proximate annular flange 166. In the exemplary embodiment illustrated in FIGS. 4-6, outer surface 146 can define an annular groove 174 adjacent flange 166 and configured to receive a portion of first sealing member 170 therein such that the first sealing member 170 can be in engagement with annular groove 174 and flange 166.

The outer surface 146 of upper member 122 can carry the target 92. In one exemplary embodiment, the target 92 can be formed of a ferromagnetic material appropriate for magnetically inducing or varying a current into circuitry 96, as will be discussed in greater detail below. The target 92 can assume a variety of sizes and shapes, but generally can have an annular form so as to encircle the tubular member 138. In the exemplary embodiment illustrated in FIGS. 4-6, target 92 can have an outer diameter equal to or substantially equal to the outer diameter of annular flange 166. In this regard, target 92 can extend longitudinally from annular flange 166 toward upper end 158 of tubular member 138. In one exemplary embodiment, target 92 can extend to the upper end 158.

In the exemplary embodiment illustrated, lower member 126 of plunger assembly 88 can be provided in the form of a shaft 182 having body 186 defining a first or lower end 190 and an opposite second or upper end 194. The body 186 can be formed of a hardened and generally non-ferromagnetic material, such as titanium or a polymeric material, that is otherwise compatible with the therapeutic substance 18 contained within internal region 72. The lower end 190 can be fixed to the base wall 68, such as by laser welding, and the body 186 can extend through aperture 162 such that the upper end 194 is positioned on an opposite side of internal wall 150 as the lower end 190.

In one exemplary embodiment, the body 186 of lower member 126 can include an increased thickness portion 198 at the upper end 194 configured to support one side of a second sealing member 202, as will be discussed in greater detail below. In this regard, body 186 can also define an annular groove 206 proximate the increased thickness portion 198 configured to receive a portion of second sealing member 202 therein. In one exemplary embodiment, the increased thickness portion 202 can cooperate with annular groove 206 to form a shoulder for supporting sealing member 202. The increased thickness portion 198 can include a longitudinal projection 210 extending longitudinally therefrom and configured to aid in locating and/or guiding the lower member 126 relative to the second closed end 118 of cap member 84. In this regard, in one exemplary embodiment, the second end 118 can include a corresponding locating feature 214 projecting from second end 118 and defining an internal recess 218 configured to nestingly receive projection 210 when reservoir 34 is in an empty or substantially empty or depleted state, as will also be discussed in greater detail below.

In one exemplary embodiment, the upper biasing member 130 can be an upper spring 226 having a first predetermined spring rate or stiffness and the lower biasing member 134 can be a lower spring 230 having a second predetermined spring rate or stiffness. The upper spring 226 can include a first end 234 positioned into upper member 122 via upper end 158 and a second end 238 in engagement with second end 118 of cap member 84. In the exemplary embodiment illustrated in FIGS. 4-6, the first end 234 can engage an upper side 242 of internal wall 150 of tubular member 138, and the second end 238 can engage and be retained by the locating feature 214 extending from the second end 118 of cap member 84. It is appreciated that second end 238 can be retained by other means than optional locating feature 214.

In a similar manner, the lower spring 230 can include a first end 248 in engagement with the lower end 190 of lower member 126 and/or base wall 68, and a second opposite end 252 in engagement with a second opposite side 256 of internal wall 150 and can be positioned around the lower member 126. In one exemplary embodiment, the lower spring 230 can have a larger inner diameter or width such that the lower member 126 can move relative to the lower spring 230. In the exemplary embodiment illustrated, the upper and lower springs 226, 230 can extend along the same longitudinal axis 260, as shown for example in FIG. 5A. In one exemplary embodiment, the upper and lower members 122, 126 and the upper and lower springs 226, 230 can be concentric about longitudinal axis 260. In this regard, the upper member 122 of plunger assembly 88 can be suspended at a center of the stacked upper and lower springs 226, 230, as shown for example in FIG. 5A.

This configuration of plunger assembly 88 can facilitate the lower member 126 telescopically moving relative to the upper member 122 in a predictable manner as the base wall 68 moves with a change in the volume of the internal region 72 of reservoir 34, as will be discussed in greater detail below. Briefly, however, the dual plunger configuration (e.g., upper or outer and lower or inner telescoping members 122, 126) in conjunction with the associated upper and lower springs 226, 230 can provide for reducing the overall travel range of the plunger assembly 88 and thereby facilitate using a more compact or thinner implantable infusion device 10. In other words, for example, a thickness of housing 26 can be reduced to provide for a lower profile implantable infusion device 10. In this regard, the upper member 122 can be configured to move at a predetermined fraction of the travel of lower member 126 based on the selected spring rate of the upper spring 226 relative to the lower spring 230, as will also be discussed below in greater detail.

With continuing reference to FIGS. 4-6 and additional reference to FIGS. 7-9, the target 92 and circuitry 96 will now be discussed in greater detail. As discussed above, target 92 can be indirectly coupled to the base wall 68 via plunger assembly 88, and thus can move with movement of the base wall 68. Conversely, the cap member 84 can be mounted to the bulkhead 64, and thus can remain stationary with movement of the base wall 68 and/or plunger assembly 88. Thus, a known relationship can be established between a longitudinal position of the target 92 relative to the passage 110 and a position of bulkhead 64 relative to the base wall 68. Because a volume (or "current volume") of the reservoir 34 can be defined as a function of a distance between the base wall 68 and the bulkhead 64, then, the longitudinal position of target 92 relative to passage 110 can be a function of, or can be indicative of, the current volume of the reservoir 34. With this in mind, the circuitry 96 can be configured to sense and/or provide information indicative of the position of the target 92 relative to the passage 110 and thus the current volume of reservoir 34.

In one embodiment, the circuitry 96 can include first and second secondary wire coils 262, 266, and a primary wire coil 270, each of which are schematically illustrated in FIGS. 4-6. The first and second secondary coils 262, 266 can be wound about the outer or exterior surface 120 of cap member 84. Relative to the orientation shown in FIGS. 4-6, the first secondary wire coil 262 constitutes a lower secondary coil, whereas the second secondary wire coil 266 constitutes an upper secondary coil. Regardless, each of the secondary coils 262, 266 can be formed of a material characterized as self-inducting in the presence of a magnetic body, for example the ferromagnetic target or core 92. Further, each of the secondary coils 262, 266 can have a length $L_{COIL}$ (e.g., longitudinal distance between opposing, leading and trailing sides 266A, 266B identified for the upper secondary coil 266 in FIG. 5A) that is directly related to a length of travel $L_{TRAVEL}$ associated with the base wall 68 of reservoir 34 relative to bulkhead 64, and in turn relative to a length $L_{TARGET}$ of the target 92, as discussed in greater detail below.

In one embodiment, however, lower and upper secondary coils 262, 266 can be partially overlapped or co-axially wound relative to the lengths $L_{COIL}$ thereof. The overlapped region is indicated at 268 in FIG. 5A, and has a length $L_O$. For reasons made clear below, in one embodiment, a direction of winding of the lower secondary coil 262 can be opposite that of the upper secondary coil 266. In other embodiments, the secondary coils 262, 266 can be wound in the same direction. Regardless, each of the secondary coils 262, 266 can be electrically connected to a sensing circuit or module (not shown, but can be provided as part of a controller or other circuitry otherwise conventionally provided with an implantable infusion device and/or external programmer) for measuring an output of the individual secondary coils 262, 266.

Figure 5A:
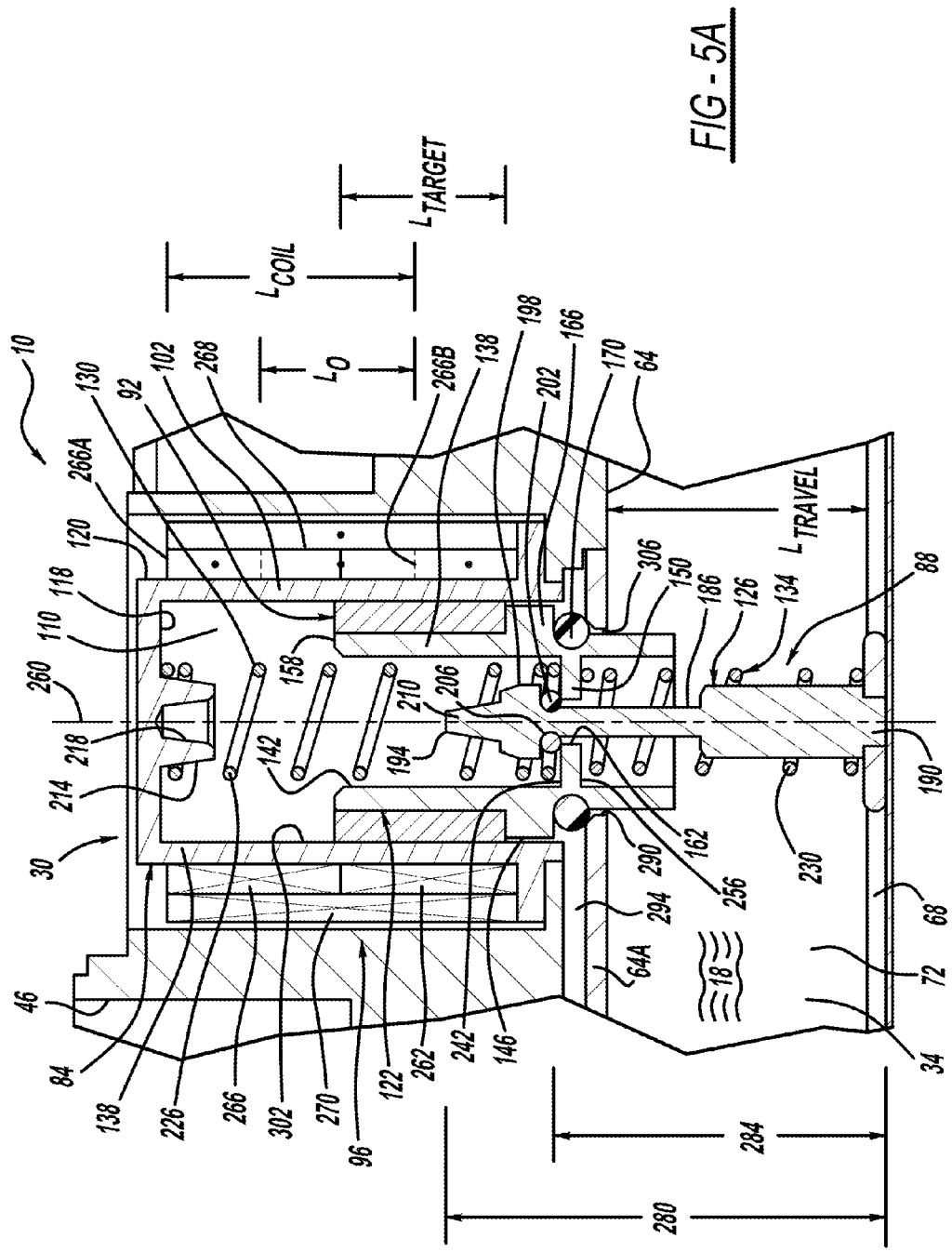
FIG. 5A is an enlarged view of a portion of the implantable infusion device of FIG. 5 in accordance with the teachings of the present disclosure.

The primary wire coil 270 can be wound about an exterior of the secondary coils 262, 266, as shown for example in FIG. 5A. In one embodiment, the primary wire coil 270 can extend a full length of the combined secondary coils 262, 266; in other embodiments, the primary wire coil 270 can have a reduced length, for example sufficient to encompass only the overlapped region 268, etc. In the exemplary embodiment illustrated, the primary wire coil 270 can be wrapped about the length $L_{COIL}$ of each of the secondary coils 262, 266. With this arrangement, a mutual inductance relationship can be created between the primary coil 270 and each of the secondary coils 262, 266 such that an electrical signal (or input signal) 274 placed across the primary coil 270 can be coupled into each of the secondary coils 262, 266. The amount of energy from the primary coil 270 actually inducted via enhanced by the presence of the ferromagnetic target 92. Thus, where the input signal 274 is an alternating current defined by a sine wave, the resultant sine wave induced in the secondary coils 262, 266, and in particular the amplitude thereof, is increased via inductance caused by the ferromagnetic target 92.

In light of the above, the circuitry 96 can be configured to effectively measure a longitudinal position of the target 92 relative to the passage 110 based upon a comparison of the output signals from the secondary coils 262, 266. For example, the two output signals from the secondary coils 262, 266 can be added to one another and processed to produce a resultant combined output signal 264 being indicative of a longitudinal position of the target 92. In the position of FIGS. 5-5A, where the reservoir 34 is shown in the full condition, the target 92 can be entirely within the lower secondary coil 262. As a result, the lower secondary coil 262 output signal can be a large, in-phase sine wave. Conversely, the target 92 is fully displaced from the upper secondary coil 266, resulting in a low output signal from the upper secondary coil 266.

Appropriate comparison of the output signal can be performed in a variety of manners. For example, in one embodiment in which the lower secondary coil 262 is wound in the same direction as the primary coil 270 and the upper secondary coil 266 is wound in the opposite direction, the output signal from the upper secondary coil 266 can be 180 degrees out of phase from that of the lower secondary coil 262. Thus, the secondary coil 262, 266 outputs 264 can be directly added to one another. Alternatively, where the secondary coils 262, 266 are wound in the same direction, the output signal from the upper secondary coil 266 can be inverted prior to comparison with the lower secondary coil 262 output (or vice versa). Regardless, in the configuration of FIG. 5A, a comparison of the lower and upper secondary coil 262, 266 outputs 264 results in a large, in-phase signal that is otherwise indicative of the target 92 being at the lower-most position, as also shown schematically in FIG. 8. This, in turn, is indicative of the base wall 68 being spaced a maximum distance from the bulkhead 64, and thus of the reservoir 34 having a current volume approximating a maximum fill amount (or 100% full). In a similar manner, when the reservoir 34 is in an empty configuration and the target 92 is adjacent the upper secondary coil 266 as shown in FIG. 6, the resultant output signal 264 can be an out of phase signal, as shown schematically in FIG. 9. Further, with the inverted or counter wound secondary coils 262, 266, the resultant output signal 264 from secondary coils 262, 266 will be flat when the reservoir 34 is in the half-full condition of FIGS. 4-4A, as schematically shown in FIG. 7. In other words, the signals from the combined coils cancel out.

In particular, as the therapeutic substance 18 is dispensed from reservoir 34, the base wall 68 can move relative to the bulkhead 64 (for example due to the positive pressure exerted thereon via the propellant chamber 38). As a result, the current volume of the reservoir 34 can be reduced. Once again, the target 92 can move relative to the passage 110 via indirect connection to base wall 68. For example, as target 92 moves from the full reservoir 34 condition shown in FIGS. 5-5A toward the empty condition shown in FIG. 6, a greater length of the target 92 can be within the lower secondary coil 262 as compared to the upper secondary coil 266. Thus, the output signal from the lower secondary coil 262 has an increased amplitude as compared to the output signal from the upper secondary coil 266. When the output signals are compared or combined, the combined signal 264 is an out-of-phase sine wave with a decreased amplitude (as compared to that associated with the combined secondary coil 262, 266 outputs when the target 92 is in the lower-most position of FIGS. 5-5A).

Thus, as the target 92 travels from the lower-most position to a mid-point of travel, the combined output signal 264 can be an in-phase sine wave of decreasing amplitude. At the mid-point of travel shown in FIGS. 4-4A, then, the lower and upper secondary coil 262, 266 outputs can effectively cancel out, as shown in FIG. 7. With further upward travel of the target 92 toward the empty condition of FIG. 6, the output signal amplitude of the upper secondary coil 266 can increase while that of the lower secondary coil 262 can decrease. The combined output signal 264 can thus be a 180 degree out-of-phase sine wave (FIG. 9), the amplitude of which increases as the target 92 travels from the mid-point to the top-most position shown in FIG. 6. A further discussion of the operation of circuitry 96 is included in commonly owned U.S. Pub. No. 2007/0255259 assigned to Medtronic, Inc., the disclosure of which is hereby incorporated by reference herein. It is also appreciated that the telescoping plunger assembly 88 can be associated with alternative sensing means in lieu of the target 92 and circuitry 96 such as, for example, optical sensing means.

The circuitry 96 output can be processed, manipulated and/or provided to a clinician in a wide variety of manners. For example, the combined output signal can simply be presented to and reviewed by the clinician, and a manual evaluation performed thereof to estimate a current volume of the reservoir 34 and thus the current volume of the contained therapeutic substance 18. Alternatively, the circuitry 96 (or in other embodiments, circuitry associated with an external programmer) can be configured to correlate and/or compare the combined output signal with a base line signal to estimate or indicate a fill percentage of the reservoir 34. For example, the combined output signal can be compared with the combined output signal generated when the target 92 is in the lower-most (and/or upper-most) position that is otherwise representative of the reservoir 34 being completely filled (or completely empty). Based upon this comparison, an estimate can be made as to the current percent fill volume. In other embodiments, the combined output signal can be compared with predetermined data points (e.g., a look-up table) that otherwise correlates signal information with volumetric values. For example, the amplitude and in-phase and out-of-phase components of the combined output signal can be compared with a table establishing a known relationship between the phase/amplitude values and corresponding volumes; or the reference table can equate fill percentage with combined output signal parameters. It is also appreciated that the circuitry 96 discussed herein is but one example of a circuitry means for use with the plunger assembly 88 in accordance with principles of the present disclosure.

With continuing reference to FIGS. 4-6, operation of the volume sensor assembly 30 and, in particular, the plunger assembly 88, will now be discussed in greater detail. As briefly discussed above, the plunger assembly 88 can use the upper and lower telescoping members 122, 126 in conjunction with the upper and lower springs 226, 230 to ratio down the amount of overall travel of upper and lower members 122, 126 as compared to the amount of travel $L_{TRAVEL}$ of base wall 68 when the volume of reservoir 34 decreases from the full condition to the empty condition.

In particular, in the exemplary embodiment illustrated, the upper and lower springs 226, 230 can have an equal unloaded length and can cooperate with the internal wall 150 of upper member 122 to operatively suspend upper member 122 between the closed end 118 of cap member 84 and the base wall 68 of reservoir 34, as generally shown in FIGS. 4-5A. In this regard, in one exemplary embodiment, the internal wall 150 can be positioned relative to a longitudinal length of upper member 122 such that the springs 226, 230 can position the target 92 (that is carried by upper member 122) in alignment or substantial alignment with lower secondary coil 262 when the reservoir 34 is in a full condition (FIGS. 5-5A) and in alignment or substantial alignment with the upper secondary coil 266 when the reservoir 34 is in an empty condition (FIG. 6). In this exemplary embodiment, the target 92 length $L_{TARGET}$ can be equal or substantially equal to a non-overlapping portion of the length $L_{COIL}$ of secondary coils 262, 266. Further, a longitudinal length 280 of lower member 126 can be sized such that the longitudinal projection 210 can be received in the internal recess 218 when the reservoir 34 is in the empty condition shown in FIG. 6. In this regard, in one exemplary embodiment, the lower member 126 can be configured with longitudinal length 280 so as to limit the travel of the base wall 68 toward bulkhead 64 when the reservoir 34 is empty or substantially empty.

Similarly, a sub-length 284 (FIG. 5A) of the lower member 126 from the lower end 190 to the annular groove 206 can be sized to cooperate with the location of the internal wall 150 relative to the annular flange 166 of upper member 122 so as to position the first sealing member 170 in engagement with the internal wall 150 and the second sealing member 202 in engagement with the bulkhead 64 when the reservoir 34 is in the full condition. In this regard, in one exemplary embodiment, the upper and lower members 122, 126 of plunger assembly 88 can thus be configured to limit the travel of base wall 68 in a direction away from bulkhead 64 and thereby define a maximum travel length of base wall 68 corresponding to the full condition of reservoir 34.

In an exemplary embodiment where the upper and lower springs 226, 230 have the same spring rate or stiffness, the upper member 122 can be configured to move at one-half the travel of the lower member 126. Thus, as the therapeutic substance 18 is delivered from reservoir 34 and the base wall 68 moves from the full condition shown in FIG. 5 toward the empty condition shown in FIG. 6, both the upper and lower members 122, 126 can move in the same direction toward the closed end 118 of cap member 84. However, for a given distance of travel $L_{TRAVEL}$ of the base wall 68, the lower member 126 can travel the same given distance $L_{TRAVEL}$ while the upper member 122 can travel only one-half of that distance. As a result, the lower member 126 can telescopically move relative to both the upper member 122 and the cap member 84 during movement of the base wall 68. In the exemplary embodiment illustrated in FIGS. 4-6, the lower member 126 can be configured to telescopically move relative to and within the upper member 122, as shown for example in FIGS. 4-6.

This dual member telescoping plunger configuration can facilitate, among other things, an ability to utilize a more compact implantable infusion device 10. In this regard, for example, by reducing the travel of the upper member 122 to a predetermined fraction of the lower member 126, the length of travel of the upper member 122 can be reduced. This reduction in travel can provide for utilizing a shorter length for the primary coil 270 as well as a shorter $L_{COIL}$ for both secondary coils 262, 266 and can thus provide for using a reduced thickness or lower profile housing 26. Further, the relative movement of the lower member 126 relative to the upper member 122 can also provide for the length of passage 110 of cap member 84 being shorter than the length of travel $L_{TRAVEL}$ of the base wall 68 from the full condition (FIG. 5) to the empty condition (FIG. 6). This can be contrasted to a single plunger mechanism that can require the length of a member supporting the primary coil, as well as the primary coil, to be at least as long as the length of travel of a base wall 68 of an associated reservoir.

It should be appreciated that while the dual member plunger assembly 88 has been discussed above in connection with two springs of the same spring stiffness, the plunger assembly 88 can alternatively utilize an upper spring 226 with a different stiffness or rate than the lower spring 230 to provide a different ratio or fraction of travel of the upper member 122 relative to the lower member 126. For example, to further reduce the travel of the upper member 122 relative to the lower member 126 for a given travel distance $L_{TRAVEL}$ of base wall 68, the stiffness of the upper spring 226 can be increased relative to the lower spring 230. In this example, the upper spring 226 could include a stiffness of twice the stiffness of the lower spring 230. This configuration could therefore result in the upper member 122 traveling one-quarter of the distance of travel of the lower member 126 and base wall 68. It is appreciated that other spring stiffness configurations or ratios could be utilized to tailor the rate of travel of the upper member 122 relative to the lower member 126 to a desired ratio for a desired application. It should also be appreciated that in various embodiments the lower member 126 may not be utilized and the lower spring 230 may directly couple the base wall 68 to the internal wall 150 of upper member 122.

Figure 5B:
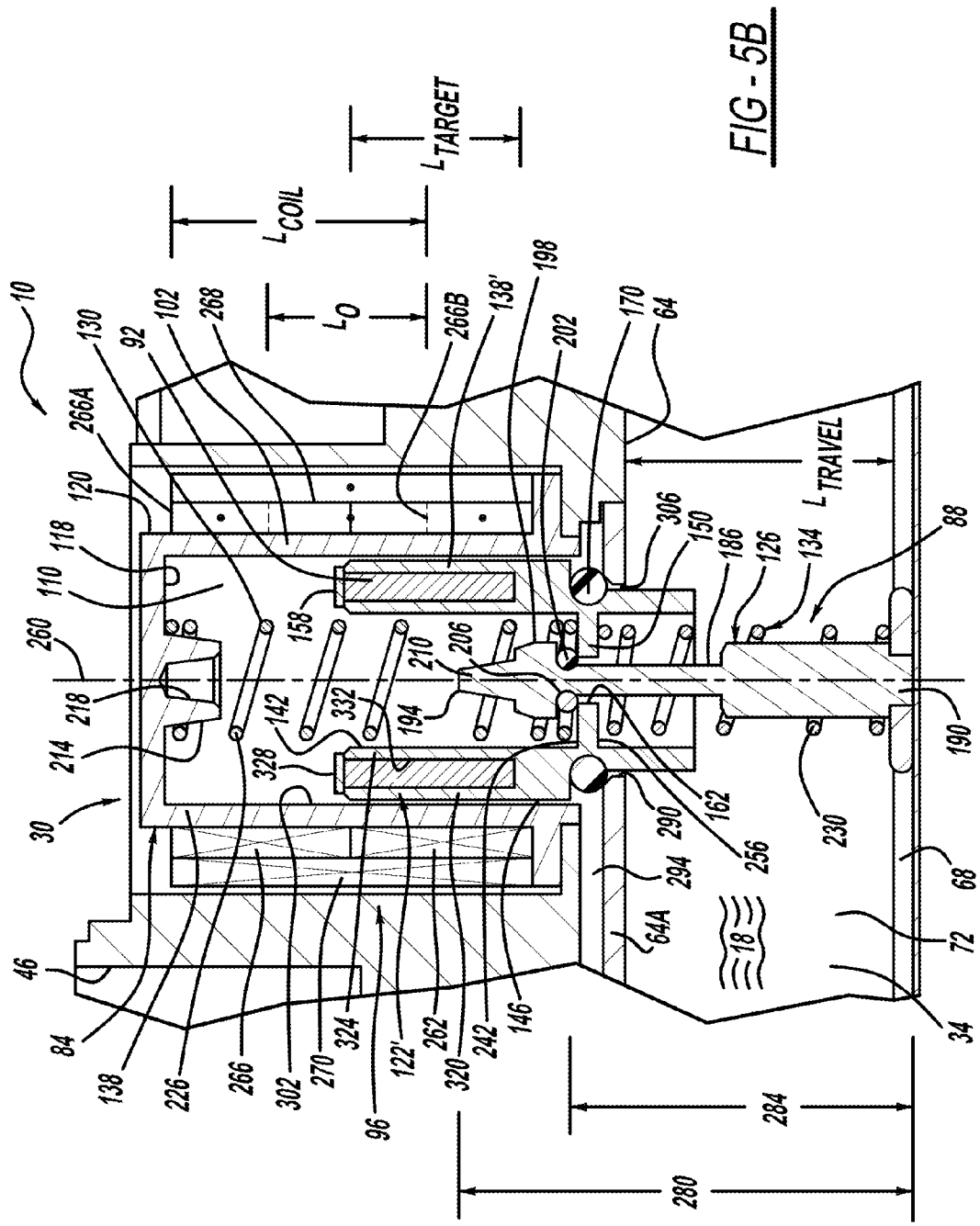
FIG. 5B is an enlarged view of a portion of the implantable infusion device of FIG. 5 illustrating an exemplary alternative volume sensing assembly in accordance with the teachings of the present disclosure.

Turning now to FIG. 5B, the volume sensor assembly 30 is shown with an exemplary alternative upper member 122'. Upper member 122' can form a hermetic enclosure or encapsulation around target 92 so as to seal off target 92 from the therapeutic substance 18, as will be discussed in greater detail below. Upper member 122' can similarly be formed of a titanium material and can include a tubular member 138' having outer and inner annular members 320, 324 spaced apart from each other to form a slot or channel 332 therebetween, as shown in FIG. 5B. The core 92 can be positioned in slot 332 and an annular cap or top member 328 can be secured to the outer and inner annular members 320, 324 to seal off target 92 from the therapeutic substance 18. In one exemplary configuration, cap member 328 can be welded to the outer and inner annular members 320, 324.

It should be appreciated that other configurations of the upper member can be used to seal off the target 92 from therapeutic substance 18. For example, the cap member 328 and the outer annular member 320 can be an integral component configured to be secured, such as be welding, to the annular flange 166 (FIG. 5A) and the inner annular member 324. Sealing off the target 92 from the therapeutic substance 18 can provide for an ability to utilize various different materials for the target 92, including materials that may not be compatible with the therapeutic fluid 18 since target 92 would be sealed off from the fluid 18 in this exemplary configuration.

The plunger assembly 88 can also serve as an overfill and/or over pressure prevention arrangement in addition to providing an ability to tailor the ratio of travel of the upper member 122 relative to the lower member 126. In this regard, and as briefly discussed above, the upper and lower members 122, 126 can be sized such that the first sealing member 170 engages the internal wall 150 relative to aperture 162, and the second sealing member 202 engages the bulkhead 64 relative to an opening or aperture 290 therethrough, as shown for example in FIG. 5A. This configuration can prevent any therapeutic substance 18 from fill port 46 entering reservoir 34, as will be discussed in greater detail below.

With initial reference to FIG. 6, a flow path from fill port 46 to reservoir 34 can be defined by implantable infusion device 10. In one exemplary embodiment, a channel 294 can extend from port 46 to a cavity 298 that is formed in housing 26 and contains cap member 84 therein. As discussed above, cap member 84 can be sealingly secured to housing 26 such that cap member 84 creates a hermetic barrier. Regardless, the therapeutic substance 18 can flow from the fill port 46 through channel 294 and into cavity 298 and/or the internal passage 110 defined by cap member 84. From there, the therapeutic substance 18 can flow into reservoir 34 via two different flow paths. The first flow path can extend from channel 294 along a space defined between an inner surface 302 of cap member 84 and outer surface 146 of tubular member 138 and an outer surface of target 92. The first flow path can then extend in an opposite direction through tubular member 138 and aperture 162 of internal wall 150 toward reservoir 34. Fluid following the first flow path can then flow through aperture 290 into reservoir 34. The second flow path can extend from channel 294 through aperture 290 into reservoir 34. In this regard, it should be appreciated that as upper member 122 extends through aperture 290 during filling of reservoir 34, a space or gap 306 (FIG. 5A) can be defined between outer surface 146 and aperture 290 such that fluid can flow therethrough. In one exemplary embodiment where aperture 290 can be utilized to provide guiding support to tubular member 138, the aperture 290 can include longitudinal grooves or splines (not shown) in a sidewall thereof to increase fluid flow in the space 306 while also providing the guiding support.

As discussed above, the upper and lower members 122, 126 of plunger assembly 88 can be sized such that the first sealing member 170 engages the internal wall 150 and the second sealing member 202 engages bulkhead 64 proximate aperture 290 when reservoir 34 is in a full condition, as shown for example in FIGS. 5-5A. In particular, the sub-length 284 of lower member 126 can be sized to bring first sealing member 170 into sealing engagement with internal wall 150 and thereby bring second sealing member 202 into sealing engagement with bulkhead 64 (and/or washer 64A) when reservoir 34 is in the full condition shown in FIGS. 5-5A. In other words, the sub-length 284 of lower member 126 can be correlated to the $L_{TRAVEL}$ so as to cooperate with the upper member 122 to bring the first and second sealing members 170, 202 into sealing engagement in the manner discussed above at the maximum $L_{TRAVEL}$ of base wall 68 of reservoir 34.

In bringing first sealing member 170 into sealing engagement with internal wall 150 when reservoir 34 is in the full condition, the plunger assembly 88 can seal off the first flow path upstream of reservoir 34 by preventing therapeutic substance 18 from flowing through aperture 162 of internal wall 150. In this regard, first sealing member 170 can include an o-ring having a larger diameter or dimension so as to extend around aperture 162 and provide a sealed connection between the increased thickness portion 198 and a surface of the internal wall 150 adjacent aperture 162, as shown for example in FIG. 5A.

Similarly, in bringing the second sealing member 202 into sealing engagement with bulkhead 64 when reservoir 34 is in the full condition, the plunger assembly 88 can also seal off the first flow path upstream of reservoir 34 by preventing the therapeutic substance 18 from flowing through aperture 290 from channel 294. In particular, sealing member 202 can include an o-ring and can form a sealed connection between annular flange 166 and/or increased thickness portion 198 and a surface of bulkhead 64 (and/or washer 64A) adjacent aperture 290 so as to prevent therapeutic substance 18 from flowing into reservoir 34 via aperture 290, as also shown for example in FIG. 5A. It is appreciated that while the implantable infusion device 10 has been discussed as having first and second flow paths in connection with channel 294, implantable infusion device 10 could alternatively include only one of the first and second flow paths along with only one of the corresponding first and second sealing members 170, 202.

The plunger assembly 88 of the present teachings can thus serve to both facilitate the use of a more compact implantable infusion device via the telescoping dual member plunger arrangement discussed herein, as well as provide protection against an overfill or over pressure condition by sealing off the flow path or paths from the fill port to the reservoir when the reservoir is in the full condition.

While one or more specific examples have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

What is claimed is:

1. A system for use in determining a volume in a reservoir, the system comprising:
    a bulkhead;
    a plunger assembly connected to the bulkhead, wherein the plunger assembly comprises
        a first plunger having a corresponding first biasing member, and
        a second plunger having a corresponding second biasing member; and
    a base of the reservoir connected to the first plunger, wherein
        movement of the base causes compression or expansion of the first biasing member, which causes compression or expansion of the second biasing member,
        the bulkhead, the first plunger, and the base define a first portion of the reservoir, and
        positions of the first plunger and the base, relative to the bulkhead, are based on the volume in the reservoir.

2. The system of claim 1, wherein:
    the first plunger is partially in the first biasing member; and
    the second biasing member is partially in the second plunger.

3. The system of claim 1, further comprising a sealing member connected to the second plunger and configured to seal with the bulkhead while the reservoir is in a full state.

4. The system of claim 1, further comprising a sealing member connected to the first plunger and configured to seal with an internal wall of the second plunger while the reservoir is in a full state.

5. The system of claim 1, further comprising:
    a channel through which a fluid is provided to the reservoir;
    a first sealing member configured to seal off the reservoir from the channel; and
    a second sealing member configured to seal off the reservoir from a cavity of the second plunger, wherein the cavity is in the bulkhead.

6. The system of claim 5, wherein:
    the first sealing member (i) seals off the reservoir from the channel while the reservoir is in a full state, and (ii) does not seal off the channel from the reservoir while the reservoir is in a depleted state; and
    the second sealing member (i) seals off the reservoir from the cavity while the reservoir is in the full state, and (ii) does not seal off the reservoir from the cavity while the reservoir is in the depleted state.

7. The system of claim 1, further comprising a bellows assembly connected to the bulkhead on a first side of the bellows assembly, wherein:
    the bellows assembly includes the base;
    the base is on a second side of the bellows assembly opposite the bulkhead; and
    the bellows assembly defines a second portion of the reservoir.

8. The system of claim 1, wherein:
    the second plunger comprises an internal wall;
    the first biasing member is on a first side of the internal wall;
    the second biasing member is on a second side of the internal wall; and
    the second biasing member has a different stiffness than the first biasing member such that, during movement of the first plunger or the second plunger, a first distance traveled by the internal wall is a predetermined fractional amount of a second distance traveled by the base.

9. The system of claim 8, wherein:
    the first biasing member is configured to be compressed between the first side of the internal wall and the base;
    the bulkhead comprises a cavity corresponding to the second plunger; and
    the second biasing member is configured to be compressed between the second side of the internal wall and a closed end of the cavity.

10. The system of claim 1, further comprising a circuit configured to generate position information indicating a position of a target, wherein the position of the target indicates a position of the second plunger.

11. The system of claim 1, further comprising a pump metering device configured to transfer a fluid between the reservoir and a catheter.

12. A method for use in determining a volume in a reservoir, the method comprising:
    transferring a fluid between a fill port and the reservoir;
    moving a base of the reservoir based on the transfer of the fluid;
    based on the movement of the base, displacing a first plunger connected to the base, wherein the first plunger has a corresponding first biasing member; and
    based on movement of the first plunger, displacing a second plunger having a corresponding second biasing member,
    wherein
        the movement of the base causes compression or expansion of the first biasing member, which causes compression or expansion of the second biasing member,
        a bulkhead, the first plunger, and the base define a first portion of the reservoir, and
        positions of the first plunger and the base, relative to the bulkhead, are based on the volume in the reservoir.

13. The method of claim 12, wherein:
    the first plunger is partially in the first biasing member; and
    the second biasing member is partially in the second plunger.

14. The method of claim 12, further comprising displacing a sealing member connected to the second plunger to seal the second plunger to the bulkhead while the reservoir is in a full state.

15. The method of claim 12, further comprising displacing a sealing member connected to the first plunger to seal an internal wall of the second plunger while the reservoir is in a full state.

16. The method of claim 12, further comprising:
transferring the fluid from the fill port through a channel to the reservoir;
displacing a first sealing member to seal off the reservoir from the channel; and
displacing a second sealing member to seal off the reservoir from a cavity of the second plunger, wherein the cavity is in the bulkhead.

17. The method of claim 16, wherein:
while the reservoir is in a full state, the first sealing member is positioned to seal off the reservoir from the channel;
while the reservoir is in a depleted state, the first sealing member is positioned not to seal off the channel from the reservoir;
while the reservoir is in the full state, the second sealing member is positioned to seal off the reservoir from the cavity; and
while the reservoir is in the depleted state, the second sealing member is positioned not to seal off the reservoir from the cavity.

18. The method of claim 12, wherein:
the second plunger comprises an internal wall;
the first biasing member is on a first side of the internal wall;
the second biasing member is on a second side of the internal wall; and
the second biasing member has a different stiffness than the first biasing member such that, during movement of the first plunger or the second plunger, a first distance traveled by the internal wall is a predetermined fractional amount of a second distance traveled by the base.

19. The method of claim 18, further comprising:
compressing the first biasing member between the first side of the internal wall and the base,
wherein the bulkhead comprises a cavity corresponding to the second plunger; and
compressing the second biasing member between the second side of the internal wall and a closed end of the cavity.

20. The method of claim 12, further comprising generating position information indicating a position of a target, wherein the position of the target indicates a position of the second plunger.

21. The method of claim 12, further comprising pumping the fluid between the reservoir and a catheter.

22. A system for determining a volume in a reservoir, the system comprising:
a sensor assembly comprising
a first plunger comprising a first sealing member and having a corresponding first biasing member,
a second plunger disposed in a cavity, wherein the second plunger comprises a second sealing member and has a corresponding second biasing member, and wherein a portion of the second plunger is disposed between the first biasing member and the second biasing member, and
a base of the reservoir, wherein the volume in the reservoir varies, and
wherein the first plunger is connected to the base and is configured to move with the base; and
a circuit configured to, based on operation of the sensor assembly, generate position information indicating a position of a target,
wherein
the target is connected to the second plunger,
a position of the base relative to a bulkhead is representative of the volume in the reservoir,
the circuit is configured to move the first sealing member and the second sealing member into sealing positions to seal off fluid communication between (i) a fill port, and (ii) the reservoir or the cavity, and
the reservoir is in a full state while the first sealing member and the second sealing member are in the sealing positions.

23. The system of claim 22, wherein the circuit is configured to, while moving the first sealing member and the second sealing member:
move the first sealing member into sealed engagement with the bulkhead to seal off a first flow path from the fill port to the reservoir; and
move the second sealing member into sealed engagement with an internal wall of the second plunger to seal off a second flow path from the fill port through the second plunger to the cavity, wherein the internal wall comprises an aperture for fluid to pass between the cavity and the reservoir.

24. The system of claim 23, wherein the circuit in moving the second sealing member into sealed engagement with the internal wall causes the first plunger to move and position the first sealing member into sealed engagement with the bulkhead.

25. The system of claim 22, wherein the circuit is configured to move the first sealing member and the second sealing member away from the sealing positions while the reservoir is in a state other than the full state to open fluid communication between (i) the fill port, and (ii) the cavity and the reservoir.

26. The system of claim 22, wherein:
the circuit is configured to, during the generating of the position information, move the second plunger by increasing the volume in the reservoir to move the base away from the bulkhead; and
the movement of the base causes movement of the first plunger, which in turn causes expansion of the first biasing member.

27. The system of claim 22, wherein:
the circuit is configured to, during the generating of the position information, move the second plunger by decreasing the volume in the reservoir to move the base closer to the bulkhead; and
the movement of the base causes movement of the first plunger and compresses the first biasing member, which causes compression of the second biasing member.

28. The system of claim 22, wherein:
movement of the base causes corresponding movement of an internal wall of the second plunger; and
the second biasing member has a different stiffness than the first biasing member such that a first distance traveled by the internal wall is a predetermined fractional amount of a second distance traveled by the base.

29. The system of claim 22, wherein:
movement of the base causes corresponding movement of an internal wall of the second plunger; and
displacement of the base by a first distance causes displacement of the internal wall a second distance, wherein the second distance is equal to one-half the first distance.

* * * * *